(12) United States Patent
Kudo et al.

(10) Patent No.: US 8,333,694 B2
(45) Date of Patent: Dec. 18, 2012

(54) ILLUMINATION UNIT, ENDOSCOPE HAVING ILLUMINATION UNIT AND ILLUMINATION PROBE HAVING ILLUMINATION UNIT WHICH IS INSERTED INTO ENDOSCOPIC CHANNEL

(75) Inventors: Akira Kudo, Hachioji (JP); Takeshi Oue, Hino (JP)

(73) Assignee: Olympus Medical Systems Corp., Tokyo (JP)

( * ) Notice: Subject to any disclaimer, the term of this patent is extended or adjusted under 35 U.S.C. 154(b) by 101 days.

(21) Appl. No.: 13/084,119

(22) Filed: Apr. 11, 2011

(65) Prior Publication Data

US 2011/0230722 A1  Sep. 22, 2011

Related U.S. Application Data

(63) Continuation of application No. PCT/JP2010/067877, filed on Oct. 12, 2010.

(30) Foreign Application Priority Data

Jan. 28, 2010  (JP) .................................. 2010-017334

(51) Int. Cl.
*A61B 1/06* (2006.01)
*A61B 3/00* (2006.01)
(52) U.S. Cl. ......... 600/178; 600/177; 362/572; 362/574
(58) Field of Classification Search .................. 600/178, 600/179, 175, 177; 313/500, 46; 362/612, 362/607, 33, 235, 296.08, 572, 574, 555, 362/243
See application file for complete search history.

(56) References Cited

U.S. PATENT DOCUMENTS

| | | | | |
|---|---|---|---|---|
| 7,285,903 B2* | 10/2007 | Cull et al. | ...... | 313/500 |
| 2006/0058584 A1* | 3/2006 | Hirata | ...... | 600/179 |
| 2007/0297045 A1* | 12/2007 | Sakai et al. | ...... | 359/350 |
| 2008/0186732 A1* | 8/2008 | Awai et al. | ...... | 362/609 |
| 2008/0285257 A1* | 11/2008 | King | ...... | 362/86 |
| 2009/0225564 A1* | 9/2009 | Minoda et al. | ...... | 362/545 |
| 2009/0284810 A1* | 11/2009 | Kawai et al. | ...... | 358/475 |

(Continued)

FOREIGN PATENT DOCUMENTS

JP  A-09-265807  10/1997

(Continued)

OTHER PUBLICATIONS

International Search Report issued in International Application No. PCT/JP2010/067877 on Jan. 18, 2011 (with translation).

(Continued)

*Primary Examiner* — John P Leubecker
*Assistant Examiner* — Ronald D Colque
(74) *Attorney, Agent, or Firm* — Oliff & Berridge, PLC (57) ABSTRACT

An illumination unit includes a distal end frame member having a through opening, a plurality of illumination sections, and a holding member which is arranged in the through opening and holds the illumination sections to incline the illumination sections at a desired angle with respect an opening surface of the through opening and to form a cascade along the axial direction of the through opening. The illumination unit includes a reflective member which is configured to reflect the illumination light emitted from the illumination sections toward the opening surface, the reflective member being held by the holding member to face the illumination sections and to apply the illumination light externally emitted from the illumination sections from the inside of the through opening via the opening surface.

12 Claims, 6 Drawing Sheets

U.S. PATENT DOCUMENTS

2010/0110658 A1* 5/2010 Peifer .............................. 362/33
2010/0309159 A1* 12/2010 Roettcher .................... 345/173

FOREIGN PATENT DOCUMENTS

| | | |
|---|---|---|
| JP | A-11-305144 | 11/1999 |
| JP | A-2002-51971 | 2/2002 |
| JP | A-2004-111355 | 4/2004 |
| JP | A-2005-342299 | 12/2005 |
| JP | A-2006-310502 | 11/2006 |
| JP | A-2007-252843 | 10/2007 |
| JP | A-2009-39464 | 2/2009 |

OTHER PUBLICATIONS

Japanese Office Action issued in Japanese Patent Application No. 2011-511179 on Apr. 19, 2011 (with translation).

* cited by examiner

ILLUMINATION UNIT, ENDOSCOPE HAVING ILLUMINATION UNIT AND ILLUMINATION PROBE HAVING ILLUMINATION UNIT WHICH IS INSERTED INTO ENDOSCOPIC CHANNEL

CROSS REFERENCE TO RELATED APPLICATIONS

This is a Continuation Application of PCT Application No. PCT/JP2010/067877, filed Oct. 12, 2010, which was published under PCT Article 21(2) in Japanese.

This application is based upon and claims the benefit of priority from prior Japanese Patent Application No. 2010-017334, filed Jan. 28, 2010, the entire contents of which are incorporated herein by reference.

BACKGROUND OF THE INVENTION

1. Field of the Invention

The present invention relates to an illumination unit having a plurality of light-emitting elements, an endoscope having this illumination unit, and an illumination probe which has this illumination unit and can be inserted into an endoscopic channel.

2. Description of the Related Art

In general, to obtain an excellent observation image, an endoscope has an illumination unit which illuminates an observation target with illumination light. The illumination unit has an illumination section that emits the illumination light and an optical system. The illumination section is, e.g., a halogen lamp or a xenon lamp. Such an illumination section is arranged in a light source device connected with an endoscope. Further, the optical system has a light guide fiber and an illumination window arranged in, e.g., the endoscope. The illumination light emitted from the illumination section is led to a distal end portion of an insertion section of the endoscope through an optical system, e.g., the light guide fiber or the like from the light source device to illuminate the observation target through the optical system, e.g., the illumination window.

Furthermore, in recent years, the illumination unit having the illumination section is arranged at the distal end portion of the insertion section. In this case, the illumination section is, e.g., a light-emitting element such as an LED which illuminates the observation target with illumination light. This light-emitting element serves as a light source. Moreover, in this case, the endoscope does not need to have a built-in light guide fiber. Therefore, a diameter and a weight of the insertion section are reduced. Additionally, the illumination section, e.g., a halogen lamp or a xenon lamp does not have to be arranged in the light source device. As described above, a configuration of the endoscope and a configuration of a peripheral device of the endoscope, e.g., the light source device can be simplified.

For example, Jpn. Pat. Appln. KOKAI Publication No. 2002-51971 discloses an endoscope comprising illumination means at a scope end, the endoscope being configured to increase the amount of illumination light. In this endoscope, when a plurality of light-emitting elements are arranged on a surface of a distal end portion of an insertion section, the amount of illumination light increases.

Further, for example, Jpn. Pat. Appln. KOKAI Publication No. 2007-252843 discloses an endoscope which effectively utilizes light-emitting diode light as illumination light and reduces a cost without optical loss caused due to use of an illumination light lens. In this endoscope, when a reflection plane is arranged between a light-emitting element and a surface of a distal end portion, desired light distribution characteristics and illumination suitable for various arrangements can be obtained.

BRIEF SUMMARY OF THE INVENTION

According to an aspect of embodiments, an illumination unit includes: a hollow member having a through opening; a plurality of illumination sections configured to emit illumination light; a holding member which is arranged in the through opening and holds the illumination sections to incline the illumination sections at a desired angle with respect an opening surface of the through opening and to form a cascade along the axial direction of the through opening; and a reflective member which is configured to reflect the illumination light emitted from the illumination sections toward the opening surface, the reflective member being held by the holding member to face the illumination sections and to apply the illumination light externally emitted from the illumination sections from the inside of the through opening via the opening surface, or being arranged on an inner surface of the through opening to face the illumination sections and to apply the illumination light externally emitted from the illumination units from the inside of the through opening via the opening surface.

According to an aspect of embodiments, an endoscope includes an illumination unit.

According to an aspect of embodiments, an illumination probe includes an illumination unit, the illumination probe being configured to be inserted into an endoscopic channel.

Advantages of the invention will be set forth in the description which follows, and in part will be obvious from the description, or may be learned by practice of the invention. Advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate embodiments of the invention, and together with the general description given above and the detailed description of the embodiments given below, serve to explain the principles of the invention.

DETAILED DESCRIPTION OF THE INVENTION

Embodiments according to the present invention will now be described hereinafter with reference to the accompanying drawings.

A first embodiment will be explained with reference to FIG. 1, FIG. 2, and FIG. 3.

Figure 1:
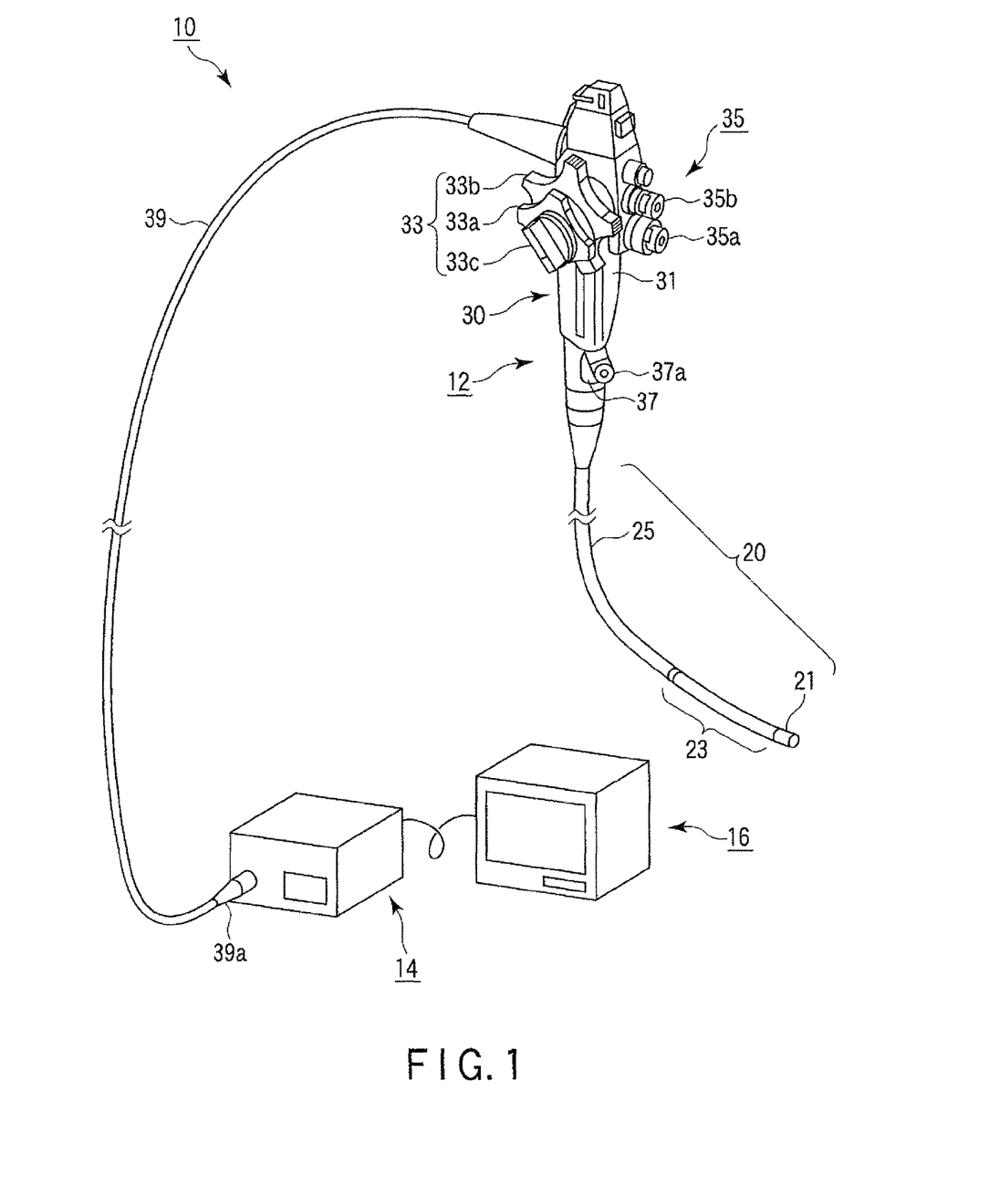
FIG. 1 is a schematic block diagram of an endoscopic system according to the present invention.

As shown in FIG. 1, an endoscopic system 10 has an endoscope 12 configured to image, e.g., a desired observation target, an image processing device 14 (e.g., a video processor) detachably connected to the endoscope 12, and a monitor 16 as a display section which is connected to the image processing device 14 and configured to display the observation target imaged by the endoscope 12. This observation target is, e.g., an affected area or a lesioned part in a subject (e.g., a body cavity).

The endoscope 12 has a hollow elongated insertion section 20 which is inserted into the subject and an operating section 30 which is arranged at a proximal end portion of this insertion section 20.

The insertion section 20 has a distal end hard section 21, a bending section 20, and a flexible tube 25 from a distal end side toward a proximal end side. A proximal end portion of the distal end hard section 21 is coupled with a distal end portion of the bending section 23, and a proximal end portion of the bending section 23 is coupled with a distal end portion of the flexible tube 25.

The distal end hard section 21 is a distal end portion of the insertion section 20.

The bending section 23 is connected to a later-described bending operating section 33 of the operating section 30 by a later-described operation wire (not shown) inserted in the flexible tube 25. The bending section 23 bends in desired directions, e.g., upper, lower, left, and right sides by operations of the bending operating section 33. When the bending section 23 bends, a position and a direction of the distal end hard section 21 change, the observation target is captured in an observation viewing field (or an imaging viewing field), and the observation target is illuminated with later-described illumination light.

It is to be noted that the bending section 23 is constituted by providing a plurality of non-illustrated substantially cylindrical (annular) node rings along the longitudinal axial direction of the insertion section 20 (the insertion direction of the endoscope 12) in parallel. The node rings adjacent to each other (placed at front and rear positions along the longitudinal axial direction of the insertion section 20) are coupled with each other by a pivot (a spindle) such as a rivet to allow their moving rotationally.

When the node rings are coupled to each other to allow their moving rotationally in this manner, the bending section 23 that can bend (moving rotationally) as described above is formed. It is to be noted that a node ring 23a arranged at a position closest to the distal end hard section 21 side is coupled with the distal end hard section 21.

The flexible tube 25 is a tubular member which has desired flexibility and is extended from the operating section 30, and it bends by external force.

Figure 2:
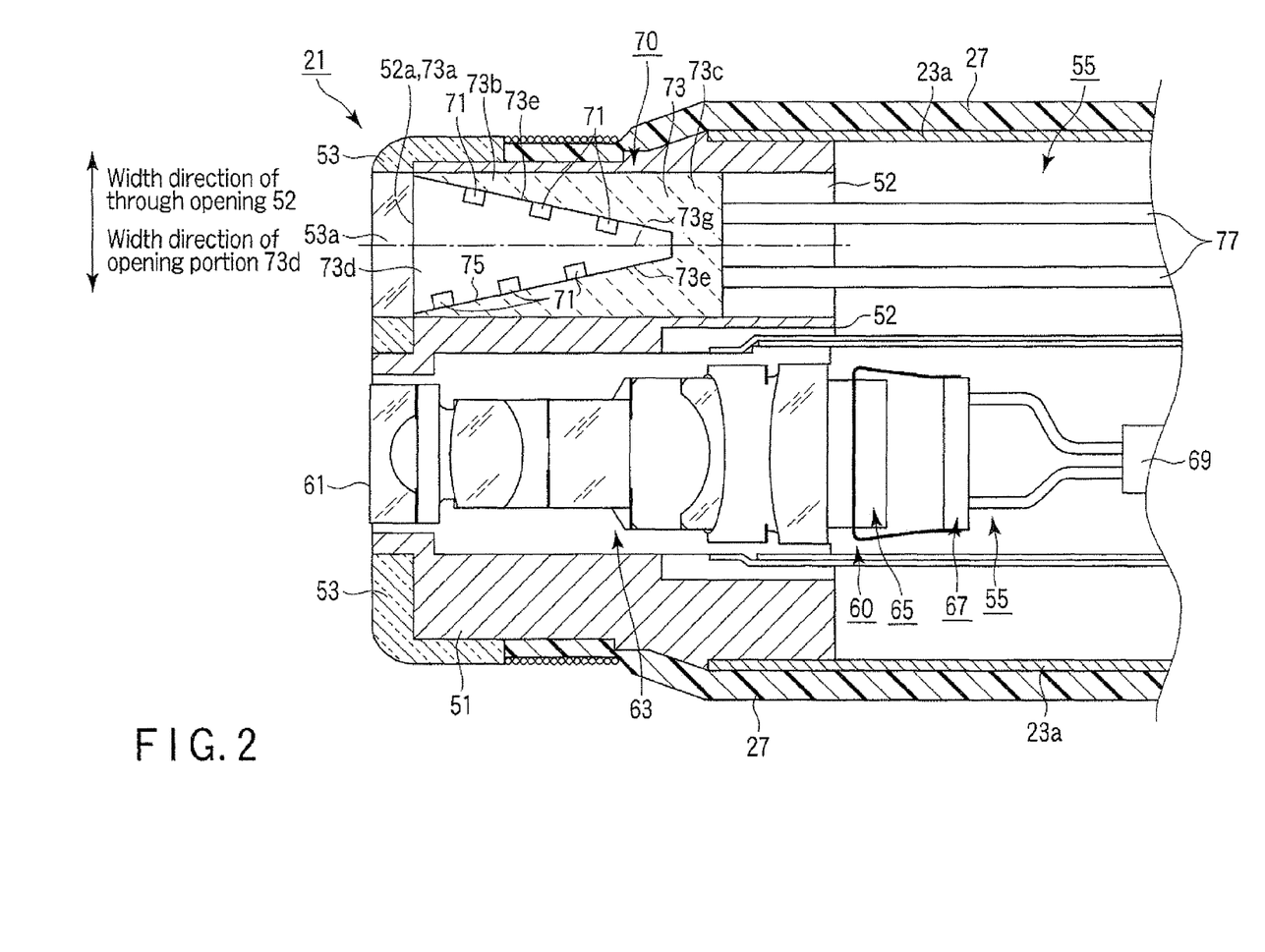
FIG. 2 is a schematic view of a distal end hard section in a first embodiment.

The distal end hard section 21 and the bending section 23 are covered with an envelope tube 27 as shown in FIG. 2. This envelope tube 27 is, e.g., a resin material and an elastic material such as rubber. Furthermore, the envelope tube 27 is formed into substantially the same shape (e.g., a hollow shape or a cylindrical shape) as the distal end hard section 21 and the bending section 23. It is to be noted that the envelope tube 27 may be injection-molded by using an elastic material having a quality of thermoplastic elastomer (e.g., a styrene base, an olefin base, or an urethane base). It is to be noted that molding of the thermoplastic elastomer is not restricted to the injection molding, and various kinds of molding methods such as cast molding, extrusion, or blow molding may be applied.

The operating section 30 has an operating section main body 31 which is a grasping section for grasping the endoscope 12 and an universal cord 39.

The bending operating section 33 which operates the bending section 33 to bend is arranged on the operating section main body 31. The bending operating section 33 has a horizontal bending operation knob 33a configured to bend the bending section 23 in the horizontal direction, a vertical bending operation knob 33b configured to bend the bending section 23 in the vertical direction, and a fixing knob 33c configured to fix a position of the bent bending section 23.

A non-illustrated bending operation mechanism for the horizontal direction which is driven by the horizontal bending operation knob 33a is connected to the horizontal bending operation knob 33a. Moreover, a non-illustrated bending operation mechanism for the vertical direction which is driven by the vertical bending operation knob 33b is connected to the vertical bending operation knob 33b. The bending operation mechanism for the vertical direction and the bending operation mechanism for the horizontal direction are arranged in the operating section 30.

The bending operation mechanism for the horizontal direction is connected to a non-illustrated operation wire inserted in the flexible tube 25 and the bending section 23, and this operation wire is connected to the bending section 23.

Additionally, the bending operation mechanism for the vertical direction is connected with a non-illustrated operation wire inserted in the flexible tube 25 and the bending section 23. The operation wire connected with the bending operation wire for the vertical direction is different from the operation wire connected with the bending operation mechanism for the horizontal direction. The operation wire connected with the bending operation mechanism for the vertical direction is connected to the bending section 23.

The horizontal bending operation knob 33a bends the bending section 23 in the horizontal direction through the bending operation mechanism for the horizontal direction and the operation wire. Further, the vertical bending operation knob 33b bends the bending section 23 in the vertical direction through the bending operation mechanism for the vertical direction and the operation wire.

Furthermore, a switch section 35 having a suction switch 35a and an air supply/water supply switch 35b is arranged on the operating section main body 31. The switch section 35 is operated by an operator's hand when the operating section main body 31 is grasped by the operator. The suction switch 35a is operated when the endoscope 12 sucks, e.g., living tissue arranged at a position close to the distal end hard section 21. The air supply/water supply switch 35b is operated when the endoscope 12 supplies air/supplies water toward this living tissue or the like.

Moreover, a medical instrument insertion section 37 is arranged on the operating section main body 31. A medical instrument insertion opening 37a is arranged in the medical instrument insertion section 37. To the medical instrument insertion opening 37a is coupled with a proximal end portion of a non-illustrated medical instrument insertion channel arranged in the insertion section 20 to extend from the flexible tube 25 to the distal end hard section 21. The medical instrument insertion opening 37a is an insertion opening through which a non-illustrated endoscopic medical instrument is inserted into the medical instrument insertion channel. The non-illustrated endoscopic medical instrument is inserted into the medical instrument insertion channel from the medical instrument insertion opening 37a. The non-illustrated endoscopic medical instrument is pushed to the distal end hard section 21 side and then protruded from a non-illustrated end opening portion of the medical instrument insertion channel arranged in the distal end hard section 21.

The universal cord 39 is extended from a side surface of the operating section main body 31. The universal cord 39 has a connector 39a that can be attached to/detached from the image processing device 14 at an end portion thereof.

The distal end hard section 21 according to this embodiment will now be described in detail with reference to FIG. 2 and FIG. 3.

As shown in FIG. 2, the distal end hard section 21 has, e.g., a stainless steel distal end frame member 51 which is coupled with the node ring 23a arranged on the endmost (the distal end hard section 21) side of the bending section 23 and a distal end portion 53 which is a distal end frame (a distal end cover) arranged to cover the distal end portion of the distal end frame member 51. The entire distal end portion 53 may be formed of a transparent material.

As shown in FIG. 2, the distal end frame member 51 is a distal end holding block which holds an imaging unit 60, an illumination unit 70, the non-illustrated medical instrument insertion channel, a non-illustrated air supply channel, and a non-illustrated water supply channel. The imaging unit 60, the illumination unit 70, the non-illustrated medical instrument insertion channel, the non-illustrated air supply channel, and the non-illustrated water supply channel are insertion members 55 inserted to reach the operating section 30 from the distal end hard section 21 via the bending section 23 and the flexible tube 25. Therefore, the distal end frame member 51 is a holding member that holds such insertion members 55. It is to be noted that the distal end frame member 51 has individual through openings 52 pierced in the longitudinal axial direction of the insertion section 20 in order to hold the respective insertion members 55. When the insertion members 55 are inserted and arranged in the respective through openings 52, the distal end frame member 51 holds the insertion members 55, respectively. That is, the distal end frame member 51 is a bored hollow member.

A non-illustrated distal end opening portion of the medical instrument insertion channel is arranged in the distal end portion 53.

The imaging unit 60 will now be described with reference to FIG. 2.

As shown in FIG. 2, the imaging unit 60 has an observation window 61, an objective optical system 63 (a lens system) which is an object lens group having predetermined field distortion, an imaging element 65 such as a CCD arranged at an image forming position of the objective optical system 63, and a connection circuit substrate 67.

The observation window 61, the objective optical system 63, the imaging element 65, and the connection circuit substrate 67 are arranged in the distal end hard section 21 in an order starting from the observation window 61 along the longitudinal axial direction of the insertion section 20 from the distal end portion 53 toward the operating section 30. In more detail, the observation window 61 is arranged in the distal end portion 53. Further, the objective optical system 63 (a lens system), the imaging element 65, and the connection circuit substrate 67 are integrated and arranged in the distal end frame member 51 (the through opening 52).

A cable 69 such as a signal line is connected to the connection circuit substrate 67. The cable 69 is inserted to reach the connector 39a via the bending section 23, the flexible tube 25, the operating section 30, and the universal cord 39. The cable 69 is included in the insertion member 55. When the connector 39a is connected to the image processing device 14, the cable 69 is connected to the image processing device 14, and the observation target imaged by the imaging unit 60 is displayed in the monitor 16.

It is to be noted that, in the objective optical system 63, at least some of lenses may be movable along the longitudinal axial direction of the insertion section 20. As a result, the imaging element 65 can take an image of the observation target in a state that the image of the observation target is focused on the imaging element 65.

Furthermore, a distal end portion of a non-illustrated image guide fiber may be fixed in placed of the imaging element 65, and the endoscope 12 may be a fiber scope without being restricted to an electronic scope.

The illumination unit 70 will now be described with reference to FIG. 2 and FIG. 3.

As shown in FIG. 2, the illumination unit 70 has the distal end frame member 51 which serves as the hollow member since the through openings 52 are formed, a plurality of illumination sections 71 that emit illumination light, a holding member 73 that is arranged in the through opening 52, and holds the illumination sections 71 therein to inclines the illumination sections 71 at a desired angle with respect to an opening surface 52a of the through opening 52, and to form a cascade along the axial direction of the through opening 52, and a reflective member 75 that is held by the holding member 73 to face the illumination sections 71 and reflects the illumination light emitted from the illumination sections 71 toward the opening surface 52a so that the illumination light emitted from the illumination sections 71 is externally applied from the inside of the through opening 52 (the holding member 73) through the opening surface 52a.

Figure 3:
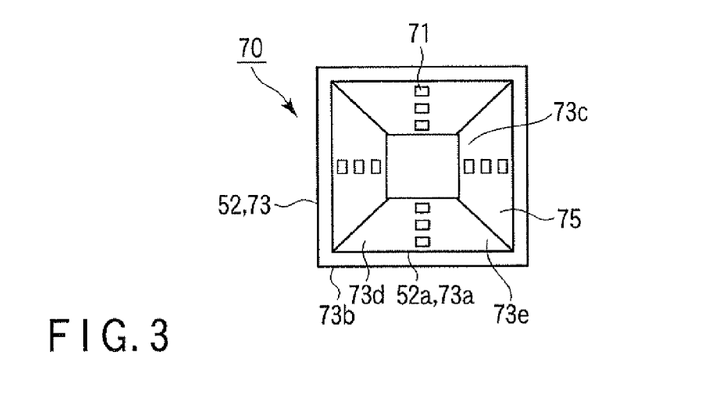
FIG. 3 is a front view of an illumination unit.

As shown in FIG. 2 and FIG. 3, the through opening 52 has, e.g., a quadrangular prism shape.

The illumination section 71 is a light-emitting element such as an LED, and it is a light source. The illumination light emitted from the illumination section 71 is, e.g., white light. As shown in FIG. 2 and FIG. 3, the illumination sections 71 are held by the holding member 73 to form a cascade along the axial direction of the through opening 52 (the longitudinal axial direction of the insertion section 20/direction of a central axis 73g of the holding member 73). Furthermore, as shown in FIG. 2, the illumination sections 71 are held by the holding member 73 in a zigzag pattern in the width direction without facing each other in the width direction of the through opening 52 (the width direction of a later-described opening portion 73d in the holding member 73) orthogonal to the axial direction of the through opening 52 so that the illumination light can be applied to the reflective member 75 rather than the other illumination sections 71. Such illumination sections 71 are arranged on an inner peripheral surface 73e of the opening portion 73d.

As shown in FIG. 2 and FIG. 3, the holding member 73 has the tapered opening portion 73d that is narrowed from a distal end portion 73b of the holding member 73 toward a proximal end portion 73c of the holding member 73 along the axial direction of the through opening 52 (the longitudinal axial direction of the insertion section 20/direction of the central axis 73g of the holding member 73). In other words, the holding member 73 is a tapered concave portion that is narrowed (reduced in diameter, for example) from the distal end portion 73b toward the proximal end portion 73c. The opening portion 73d has, e.g., a substantially truncated quadrangular pyramid shape as shown in FIG. 3. A taper angle is adjusted to a desired angle.

When the holding member 73 is arranged in the through opening 52, the distal end portion 73b abuts on the opening surface 52a of the through opening 52. An opening surface 73a of the opening portion 73d (the holding member 73) has the same size as that of the opening surface 52a of the through opening 52, and it is also the opening surface 52a of the through opening 52. Therefore, the opening surface 73a is arranged on the same level as the opening surface 52a.

Moreover, the holding member 73 is detachably inserted into the through opening 52. As shown in FIG. 3, the holding member 73 has a quadrangular prism shape to be inserted into the through opening 52 having a quadrangular prism shape. That is, the outer shape of the holding member 73 is substantially equal to the inner shape of the through opening 52. When the holding member 73 is inserted into the through opening 52, the holding member 73 is engaged with the through opening 52.

The holding member 73 is formed of, e.g., ceramic having thermal conductivity. A cover member 53a is arranged on the distal end portion 53 to face the opening surfaces 52a and 73a. The cover member 53a is formed of a transparent member such as glass through which the illumination light can be transmitted or a synthetic resin through which the illumination light can be transmitted. A size of the cover member 53a is substantially equal to sizes of the opening surfaces 52a and 73a.

As shown in FIG. 2 and FIG. 3, the holding member 73 directly holds the plurality of illumination sections 71 and the reflective member 75 on the inner peripheral surface 73e of the opening portion 73d (the holding member 73).

In more detail, the holding member 73 directly holds the plurality of illumination sections 71 on the inner peripheral surface 73e so that they can be inclined at a desired angle with respect to the opening surfaces 52a and 73a and face the inner peripheral surface 73e. As descried above, the illumination sections 71 are arranged in the holding member 73.

It is to be noted that the holding member 73 (the opening portion 73d) has the tapered shape as described above, and hence it holds the illumination sections 71 in such a manner that the illumination sections 71 arranged on the proximal end portion 73c side are arranged closer to the central axis 73g side than the illumination sections 71 arranged on the distal end portion 73b side. That is, as shown in FIG. 3, when the holding member 73 is seen from the front side, the holding member 73 holds the illumination sections 71 in such a manner that the illumination sections 71 radially spread from the proximal end portion 73c side (the inner/central side) toward the distal end portion 73b side (the front/end side).

Further, as shown in FIG. 2 and FIG. 3, the holding member 73 holds the illumination sections 71 in such a manner that the illumination sections 71 form the cascade along the axial direction of the through opening 52 (the longitudinal axial direction of the insertion section 20/direction of the central axis 73g of the holding member 73) and the illumination sections 71 form the zigzag pattern in the width direction without facing each other in the width direction of the opening portion 73d (the through opening 52) as described above.

Furthermore, the holding member 73 directly holds the reflective member 75 on the inner peripheral surface 73e so that the illumination sections 71 emit the illumination light toward the reflective member 75. In more detail, the holding member 73 holds the reflective member 75 in such a manner that the reflective member 75 reflects the illumination light emitted from the illumination sections 71 held on the proximal end portion 73c side toward the opening surfaces 52a and 73a rather than the illumination sections 71 held on the distal end portion 73b side.

At this time, the reflective member 75 reflects the illumination light emitted from the illumination sections 71 toward the external observation target from the inside of the holding member 73 via the opening surfaces 52a and 73a and the cover member 53a.

Moreover, the reflective member 75 is arranged on the entire inner peripheral surface 73e as described above. Additionally, since the opening portion 73d has the tapered shape, the reflective member 75 arranged on the entire inner peripheral surface 73e likewise has a tapered shape that is narrowed from the distal end portion 73b toward the proximal end portion 73c along the axial direction of the through opening 52 (the longitudinal axial direction of the insertion section 20/direction of the central axis 73g of the holding member 73) in accordance with the shape of the opening portion 73d.

Further, since the reflective member 75 is arranged on the inner peripheral surface 73e, it is arranged on the same level as the illumination sections 71. Therefore, in this embodiment, the illumination sections 71, the holding member 73, and the reflective member 75 are integrated.

It is to be noted that a non-illustrated conducting section is laminated on the reflective member 75. The conducting section has a non-illustrated conductor pattern formed of, e.g., a copper foil. Furthermore, the illumination sections 71 are arranged on this conducting section. Non-illustrated lead wires of anodes and cathodes of the illumination sections 71 are electrically connected with conductor patterns serving as respective corresponding conduction paths.

Moreover, a non-illustrated conducting section is laminated on the proximal end portion 73c of the holding member 73. This conducting section has a non-illustrated conductor pattern formed of, e.g., a copper foil. A part of the conducting section of the reflective member 75 is inserted into the holding member 73 to be electrically connected with the conducting section of the proximal end portion 73c and thereby connected to illumination electrical wires 77 associated with the anodes and cathodes of the illumination sections 71.

The illumination electrical wires 77 have thermal conductivity. Since the illumination electrical wires 77 have thermal conductivity, it is preferable for these wires 77 to have large diameters for radiation of heat generated by the illumination sections 71.

The illumination wires 77 are inserted to reach the connector 39a via the bending section 23, the flexible tube 25, the operating section 30, and the universal cord 39. When the connector 39a is connected with the image processing device 14, the illumination electrical wires 77 are connected to the image processing device 14, and the image processing device 14 controls the illumination.

An operation method according to this embodiment will now be described.

As shown in FIG. 2, the holding member 73 directly holds the plurality of illumination sections 71 and the reflective member 75 on the inner peripheral surface 73e. At this time, as shown in FIG. 2 and FIG. 3, the holding member 73 is arranged in the through opening 52 in a state that the illumination sections 71 are held in such a manner that the illumination sections 71 form the cascade along the axial direction of the through opening 52 (the longitudinal axial direction of the insertion section 20/the central axis 73g of the holding member 73) and form the zigzag pattern in the width direction of the opening portion 73d. At this time, the holding member 73 is engaged with the through opening 52, the distal end portion 73b abuts on the opening surface 52a, and the opening surface 52a and the opening surface 73a communicate with each other.

As shown in FIG. 1, when the connector 39a is connected with the image processing device 14, the insertion section 20 is inserted into a body cavity, and the bending operating section 33 is operated, the bending section 23 bends. As a result, a position and a direction of the distal end hard section 21 vary, the imaging unit 60 captures the observation target in the observation viewing field (or the imaging viewing field), and the illumination unit 70 illuminates the observation target with the illumination light.

At this time, the respective illumination sections 71 emit the illumination light. This illumination light is not directly applied to the observation target through the opening surfaces 52a and 73a and the cover member 53a, but they are applied to the reflective member 75 from the illumination sections 71. Furthermore, for example, the illumination light is reflected by the reflective member 75 once, whereby the observation target is illuminated through the opening surfaces 52a and 73a and the cover member 53a.

It is to be noted that the holding member 73 has the opening portion 73d having the tapered shape narrowed from the distal end portion 73b toward the proximal end portion 73c along the direction of the central axis 73g. Moreover, the holding member 73 directly holds the illumination sections 71 and the reflective member 75 on the inner peripheral surface 73e. Therefore, when illuminating the observation target with the illumination light through the opening surfaces 52a and 73a and the cover member 53a, the illumination light is applied to the observation target in a state that the directionality is assured without being narrowed down.

Additionally, the holding member 73 directly holds the plurality of illumination sections 71 on the inner peripheral surface 73e in such a manner that the illumination sections 71 are inclined at a desired angle with respect to the opening surfaces 52a and 73a and they face the inner peripheral surface 73e, and the holding member 73 directly holds the reflective member 75 on the inner peripheral surface 73e in such a manner that the illumination sections 71 illuminate the reflective member 75 with the illumination light. Further, the reflective member 75 is arranged on the entire inner peripheral surface 73e and has the tapered shape narrowed from the distal end portion 73b toward the proximal end portion 73c along the longitudinal axial direction of the insertion section 20 in accordance with the shape of the opening portion 73d. Therefore, the reflective member 75 reflects the illumination light emitted from the illumination sections 71 toward the opening surfaces 52a and 73a in a state that a desired amount of light is effectually assured. Furthermore, the observation target is illuminated with the illumination light through the opening surfaces 52a and 73a and the cover member 53a in a state that the desired amount of light is assured.

Moreover, the illumination sections 71 are arranged on the inner peripheral surface 73e so that the illumination sections 71 radially spread toward the distal end portion 73b side (the front/end side) from the proximal end portion 73c side (the inner/central side) in accordance with the shape of the opening portion 73d as shown in FIG. 3. Additionally, the illumination sections 71 are arranged on the inner peripheral surface 73c in such a manner that they form the cascade along the axial direction of the through opening 52 (the longitudinal axial direction of the insertion section 20/direction of the central axis 73g of the holding member 73) and form the zigzag pattern in the width direction without facing each other in the width direction of the opening portion 73d as shown in FIG. 2.

As a result, the illumination light emitted from the illumination sections 71 held on the proximal end portion 73c side is assuredly reflected by the reflective member 75 toward the opening surfaces 52a and 73a rather than the illumination sections 71 held on the distal end portion 73b side. Further, the observation target is assuredly illuminated with the illumination light emitted from the illumination sections 71 arranged on the proximal end portion 73c side and reflected toward the opening surface 52a and 73a by the reflective member 75 without blocking the illumination light by the illumination sections 71 arranged on the distal end portion 73b side.

As a result, the observation target is effectually illuminated with all the illumination light through the opening surfaces 52a and 73a and the cover member 53a in a state that a desired amount of light is assured.

As described above, the observation target is effectually illuminated with the illumination light in a state that the desired amount of light is assured.

Further, the holding member 73 directly holds the illumination sections 71 and the reflective member 75 on the inner peripheral surface 73e. Therefore, when the holding member 73 is arranged in the through opening 52, the illumination sections 71 and the reflective member 75 are arranged all together in the distal end frame member 51.

Furthermore, since the holding member 73 is engaged with the through opening 52, it is not displaced, and the illumination light does not blur.

Moreover, when the illumination sections 71 emit the illumination light, the illumination sections 71 radiate heat. This heat is externally radiated by the holding member 73 having thermal conductivity. Additionally, this heat is also externally radiated by the illumination electrical wires 77 having thermal conductivity.

As descried above, in this embodiment, the holding member 73 holds the plurality of illumination sections 71 in such a manner that the plurality of illumination sections 71 are inclined at a desired angle with respect to the opening surfaces 52a and 73a, face the inner peripheral surface 73e, form the cascade along the direction of the central axis 73g of the holding member 73, and form the zigzag pattern in the width direction without facing each other in the width direction of the opening portion 73d.

Further, in this embodiment, the holding member 73 holds the reflective member 75 so that the reflective member 75 can face the illumination sections 71.

Furthermore, in this embodiment, the reflective member 75 reflects the illumination light emitted from the illumination sections 71 toward the opening surfaces 75a and 73a so that the illumination light emitted from the emitting sections 71 can be externally applied from the inside of the through opening 52 (the holding member 73) via the opening surfaces 52a and 73a.

As described above, in this embodiment, even if the plurality of illumination sections 71 are arranged, the diameter of the distal end hard section 21 which is the distal end portion of the insertion section 20 is not increased depending on how the plurality of illumination sections 71 and the reflective member 75 are arranged and how the reflective member 75 reflects the light, and the plurality of illumination sections 71 as the light-emitting elements can be arranged to readily assure a desired amount of light.

Furthermore, in this embodiment, the illumination sections 71 and the reflective member 75 are directly arranged on the inner peripheral surface 73e, and the opening portion 73d has the tapered shape that is narrowed from the distal end portion 73b toward the proximal end portion 73c along the direction of the central axis 73g, whereby the observation target can be efficiently illuminated in the state that the directionality can be assured without narrowing the illumination light when illuminating the observation target with the illumination light via the opening surfaces 52a and 73a and the cover member 53a.

Moreover, in this embodiment, the plurality of illumination sections 71 are directly held by the holding member 73 in such a manner that the plurality of illumination sections 71 are inclined at a desired angle with respect to the opening surfaces 52a and 73a and face the inner peripheral surface 73e, and the reflective member 75 is directly held by the holding member 73 so that the illumination sections 71 emit the illumination light toward the reflective member 75. Additionally, in this embodiment, the reflective member 75 is arranged on the entire inner peripheral surface 73e, and the reflective member 75 has the tapered shape that is narrowed toward the proximal end portion 73c from the distal end portion 73b along the direction of the central axis 73g in accordance with the shape of the opening portion 73d. As a result, in this embodiment, the illumination light can be effectually reflected toward the opening surfaces 52a and 73a by the reflective member 75, and the observation target can be effectually illuminated with the illumination light via the opening surfaces 52a and 73a and the cover member 53a while assuring a desired amount of light.

Further, in this embodiment, the illumination sections 71 are arranged to radially spread from the proximal end portion 73c side (the inner/central side) toward the distal end portion 73b side (the front/end side) in accordance with the shape of the opening portion 73d, and the illumination sections 71 are arranged to form the cascade along the direction of the central axis 73g of the holding member 73 and also form the zigzag pattern in the width direction without facing each other in the width direction of the opening portion 73d.

As a result, in this embodiment, the illumination light that is emitted from the illumination sections 71 arranged on the proximal end portion 73c side and reflected toward the opening surfaces 52a and 73a by the reflective member 75 can be prevented from being blocked by the illumination sections 71 arranged on the distal end portion 73b side.

As described above, in this embodiment, the reflective member 75 can be assuredly illuminated with the illumination light, and the illumination light emitted from the illumination sections 71 held on the proximal end portion 73c side can be assuredly reflected by the reflective member 75 toward the opening surfaces 52a and 73a rather than the illumination sections 71 held on the distal end portion 73b side. As a result, in this embodiment, the observation target can be effectually illuminated with all the illumination light via the opening surfaces 52a and 73a and the cover member 53a in a state that a desired amount of light is assured.

Although the illumination light is reflected by the reflective member 75 once in this embodiment, the present invention does not have to be restricted thereto. In this embodiment, the number of times of reflection of the illumination light is not restricted as long as the observation target can be effectually illuminated with the illumination light via the opening surfaces 52a and 73a and the cover member 53a without blocking the illumination light by the illumination sections 71 on the distal end portion 73b side in a state that a desired amount of light is assured.

Further, in this embodiment, if the observation target can be effectually illuminated with the illumination light via the opening surfaces 52a and 73a and the cover member 53a without blocking the illumination light by the illumination sections 71 on the distal end portion 73b side in a state that a desired amount of light is assured, each gap between the illumination sections 71 in the axial direction of the through opening 52, a length of the opening portion 73d in the longitudinal axial direction of the insertion section 20, the number of the illumination sections 71, and arrangement positions of the illumination sections 71 can be adjusted to desired values.

Furthermore, in this embodiment, desired light distribution characteristics can be obtained by adjusting a taper angle of the opening portion 73d, thereby illuminating the observation target with higher brightness.

Moreover, in this embodiment, the illumination sections 71 and the reflective member 75 can be arranged all together at the distal end frame member 51 by using the holding member 73, whereby assembly time for the distal end hard section 21 can be shortened.

Additionally, in this embodiment, since the holding member 73 is engaged with the through opening 52, the holding member 73 is not displaced when the endoscope 12 is being operated, thereby preventing the illumination light from blurring.

Further, in this embodiment, to arrange the plurality of illumination sections 71, a light guide fiber does not have to be included in the endoscope 12. Therefore, in this embodiment, the diameter and the weight of the insertion section 20 can be reduced. Furthermore, in this embodiment, a halogen lamp or a xenon lamp does not have to be arranged in each illumination section 71, and a light source device is not required either. Accordingly, in this embodiment, the configuration of the endoscope 12 and the configuration of the peripheral device of the endoscope 12, i.e., the endoscopic system 10 can be simplified.

Moreover, in this embodiment, since the holding member 73 has the head conductivity, a great amount of heat generated by the plurality of illumination sections 71 can be easily and efficiently released by the holding member 73.

Additionally, in this embodiment, since the illumination electrical wires 77 have thermal conductivity, heat is conducted to the illumination electrical wires 77 via the holding member 73, thereby obtaining a thermal radiation effect.

Further, in this embodiment, a large amount of heat generated by the plurality of illumination sections 71 is conducted to the illumination electrical wires 77 via the holding member 73 by increasing the diameters of the illumination electrical wires 77, thus obtaining a higher thermal radiation effect.

It is to be noted that the illumination sections 71 emit, e.g., white light, but the present invention does not have to be restricted thereto. The plurality of illumination sections 71 may emit illumination light in different color wavelength bands for, e.g., red (R), green (G), and blue (B). As a result, in this embodiment, an electronic endoscope that processes an image by a frame sequential method can be configured.

Furthermore, a regular light observation mode where regular light observation is performed may be switched to/from a special light observation mode where special light observation (narrowband imaging [NBI (registered trademark)]) is carried out to observe the observation target in the subject.

In the regular light observation, later-described regular light is used. The regular light observation means observing an observation area by using the regular light. Moreover, in the special light observation, later-described special light is used. The special light observation means observing an observation area by using the special light.

Therefore, in this embodiment, one of the plurality of illumination sections 71 can emit the regular light for the regular light observation, and the other of the plurality of illumination sections 71 can emit the special light for the special light observation.

It is to be noted that the regular light is light (white light) including light having a wavelength in a desired narrow band, which is visible light in a wavelength band of 380 nm to 750 nm including light in a narrow band of approximately 390 nm to approximately 445 nm and light in a narrow band of approximately 530 nm to approximately 550 nm and is also white light, and it includes the later-described special light.

Additionally, the special light is light having a wavelength in a desired narrow band, and it is light in a desired wavelength band centering on a desired wavelength. In this case, the special light is, e.g., light in an arrow band of approximately 390 nm to approximately 445 nm centering on a wavelength of approximately 415 nm and also light in a narrow band of approximately 530 nm to approximately 550 nm centering on a wavelength of substantially 540 nm. The former light is blue, and the latter light is green.

In the special light observation, highlighting of blood capillaries in a superficial portion of a mucous membrane or mucosal fine patterns is realized by emitting light having two narrowband wavelengths that are apt to be absorbed by hemoglobin in the blood. In general, to observe a blood vessel with high contrast, use of light that is characterized by being intensively absorbed into the blood and also characterized by being intensively reflected/scattered by the superficial portion of the mucous membrane attracts attention.

Therefore, blue narrowband light (light in a narrow band of approximately 390 nm to approximately 445 nm) for observation of blood capillaries in the superficial portion of the mucous membrane and green narrowband light (light in a narrow band of approximately 530 nm to approximately 550 nm) for enhancement of contrast between observation of thick blood vessels at a deep region and blood capillaries in the superficial portion of the mucous membrane are used.

The shapes of the holding member 73 and the opening portion 73d are not restricted in particular.

Figure 4A:
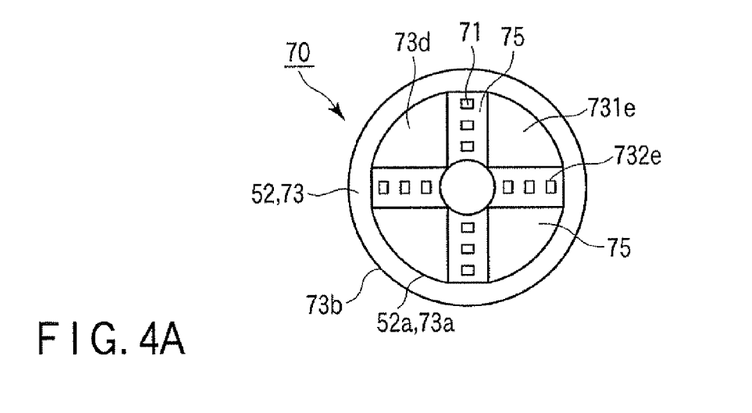
FIG. 4A is a front view of an illumination unit in a first modification.

For example, as shown in FIG. 4A, the opening portion 73d may have a substantially circular truncated cone shape. At this time, the inner peripheral surface 731e on which the reflective member 75 alone is arranged has a part of the circular truncated cone shape, and the inner peripheral surface 732e on which the illumination sections 71 and the reflective member 75 are arranged has the tapered shape.

Figure 4B:
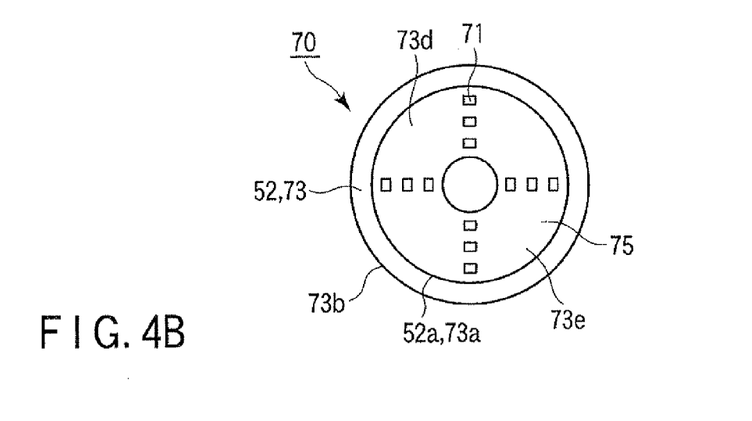
FIG. 4B is a front view of an illumination unit in a second modification.

Further, for example, as shown in FIG. 4B, the opening portion 73d may have a substantially circular truncated cone shape.

It is to be noted that each of the through opening 52 and the holding member 73 may have, e.g., a substantially cylindrical shape as shown in FIG. 4A and FIG. 4B or a prismatic shape as shown in FIG. 3.

Figure 5:
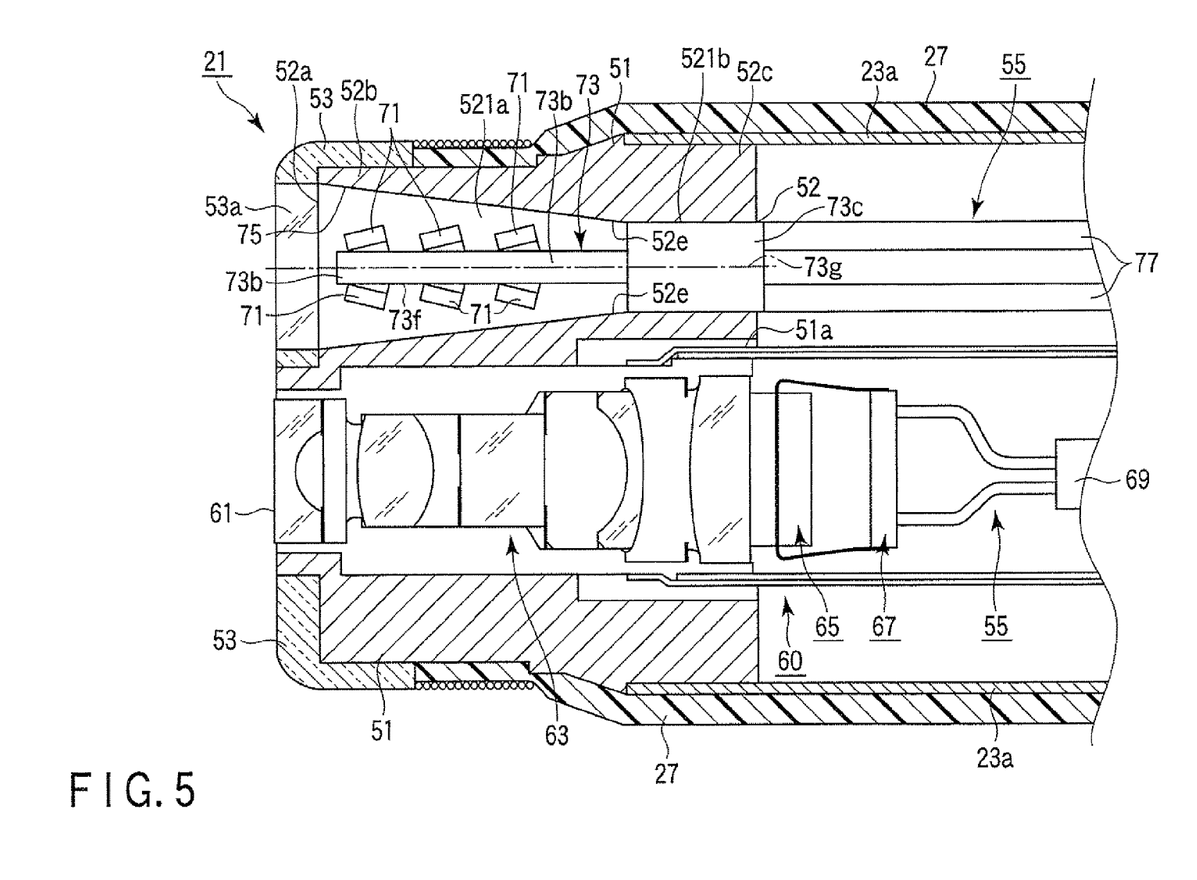
FIG. 5 is a schematic view of a distal end hard section in a second embodiment.
Figure 6:
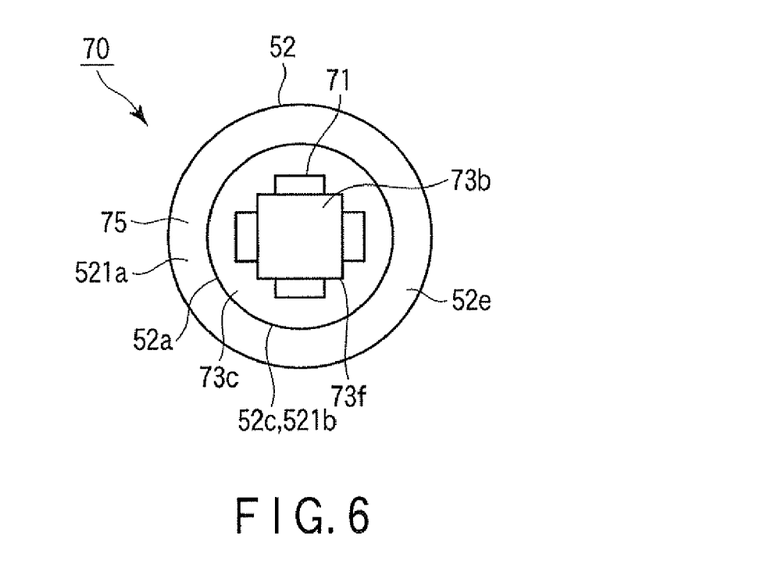
FIG. 6 is a front view of an illumination unit in the second embodiment.

A second embodiment according to the present invention will now be described with reference to FIG. 5 and FIG. 6. Structures equivalent to those in the first embodiment will be denoted by reference numbers matching those in the first embodiment, thereby omitting a description thereof.

A through opening 52 according to this embodiment in which a holding member 73 is arranged has a tapered portion 521a having a tapered shape radially narrowed from a distal end portion 52b toward a proximal end portion 52c of the through opening 52 along the axial direction of the through opening 52 and a cylindrical portion 521b communicating with the tapered portion 521a at the proximal end portion 52c. Such a through opening 52 has a funnel shape.

It is to be noted that the tapered portion 521a also has a circular truncated cone shape that is radially narrowed from the distal end portion 52b toward the proximal end portion 52c. A taper angle can be adjusted to a desired value.

The holding member 73 that has a columnar shape and holds a plurality of illumination sections 71 on an outer peripheral surface 73f is arranged in the through opening 52. The distal end portion 73b has the plurality of illumination sections 71 and can be inserted into the cylindrical portion 521b in a state that the illumination sections 71 are provided on the distal end portion 73b. The proximal end portion 73c has the same size as the cylindrical portion 521b. As a result, when arranging the holding member 73 in the through opening 52, the distal end portion 73b is inserted into the cylindrical portion 521b to be arranged in the tapered portion 521a, and the proximal end portion 73c is engaged with (supported by) the cylindrical portion 521b. In this manner, the holding member 73 is detachably positioned and fixed in the through opening 52.

The distal end portion 73b has, e.g., a quadrangular prismatic shape. The holding member 73 holds the illumination sections 71 on, e.g., four outer peripheral surfaces 73f of this distal end portion 73b in the axial direction of the through opening (the longitudinal axial direction of an insertion section 20/direction of a central axis 73g of the holding member 73) in cascade patterns. The distal end portion 73b is arranged in the tapered portion 521a as described above. Therefore, the holding member 73 holds the plurality of illumination sections 71 to face an inner peripheral surface 52e of the through opening 52 (the tapered portion 521a). The holding member 73 is formed of, e.g., ceramics having thermal conductivity.

Furthermore, a reflective member 75 is directly arranged on the inner peripheral surface 52e of the through opening 52 (the tapered portion 521a). This reflective member 75 faces the illumination sections 71, is arranged on the inner peripheral surface 52e of the through opening 52 as described above, and reflects illumination light emitted from the illumination sections 71 toward an opening surface 52a so that the illumination light emitted from the illumination sections 71 can be externally applied from the inside of the through opening 52 via the opening surface 52a.

This reflective member 75 is arranged on the entire inner peripheral surface 52e. Since the reflective member 75 is arranged on the entire inner peripheral surface 52e, it is arranged to surround the illumination sections 71. Furthermore, since the through opening 52 has the tapered portion 521a, the reflective member 75 arranged on the entire inner peripheral surface 52e also has a tapered shape radially narrowed from the distal end portion 52b toward the proximal end portion 52c along the axial direction of the through opening 52 in accordance with the through opening 52 (the tapered portion 521a).

As described above, in this embodiment, the illumination sections 71 and the holding member 73 are integrated, and they are formed separately from the reflective member 75.

An operation method according to this embodiment will now be described.

The holding member 73 is arranged in the through opening 52 in a state that the plurality of illumination sections 71 are directly held on the outer peripheral surfaces 73f in cascade patterns along the axial direction of the through opening 52 (the longitudinal axial direction of the insertion section 20/central axis 73g of the holding member 73). At this time, the distal end portion 73b is inserted into the proximal end portion 52c (the cylindrical portion 521b) to be arranged in the tapered portion 521a, and the proximal end portion 73c is engaged with (supported by) the proximal end portion 52c (the cylindrical portion 521b). As a result, the holding member 73 is detachably positioned and fixed in the through opening 52. Moreover, the reflective member 75 is arranged on the entire inner peripheral surface 52e to surround the illumination sections 71.

Additionally, a connector 39a is connected to an image processing device 14.

A subsequent operation is substantially the same as that in the first embodiment, thereby omitting a description thereof.

As described above, in this embodiment, the same effects as those in the first embodiment can be obtained.

Further, in the first embodiment, since the illumination sections 71 are on the same level as the reflective member 75, arranging the illumination sections 71 is not easy since a desired amount of light must be assured at illuminated parts of the reflective member 75 illuminated with the illumination light, and a degree of freedom of arranging the illumination sections 71 may be possibly lowered. If the illumination sections 71 are arranged on the illuminated parts, the illumination light may be applied to the illumination sections 71 and possibly blocked by the illumination sections 71.

However, in this embodiment, the illumination sections 71 are not provided on the same level as the reflective member 75, and the illumination sections 71 are held on the outer peripheral surface 73f and surrounded by the reflective member 75 to face the reflective member 75. As a result, the illumination light emitted from the illumination sections 71 is applied to the reflective member 75 without being affected by a taper angle of the through opening 52 and without being blocked. Therefore, in this embodiment, the illumination light can be prevented from being blocked by the illumination sections 71, thereby securely assuring a desired amount of light.

Further, as a result, in this embodiment, the degree of freedom of arranging the illumination sections 71 can be increased without being affected by the reflective member 75.

Furthermore, in this embodiment, since the proximal end portion 73c is supported by the proximal end portion 52c, the holding member 73 is not displaced when the endoscope 12 is being operated, thereby preventing the illumination light from blurring.

Moreover, in this embodiment, since the holding member 73 is integrated with the illumination sections 71 alone, the holding member 73 can be easily manufactured.

Additionally, in this embodiment, although the illumination sections 71 are arranged on the four outer peripheral surfaces 73f, the present invention is not restricted thereto, they may be arranged on the two outer peripheral surfaces 73f alone, or they may be arranged on six outer peripheral surfaces 73f if the holding member 73 has, e.g., a hexagonal columnar shape. As described above, in this embodiment, the illumination sections 71 can be arranged in a desired manner in accordance with the shape of the holding member 73.

Figure 7:
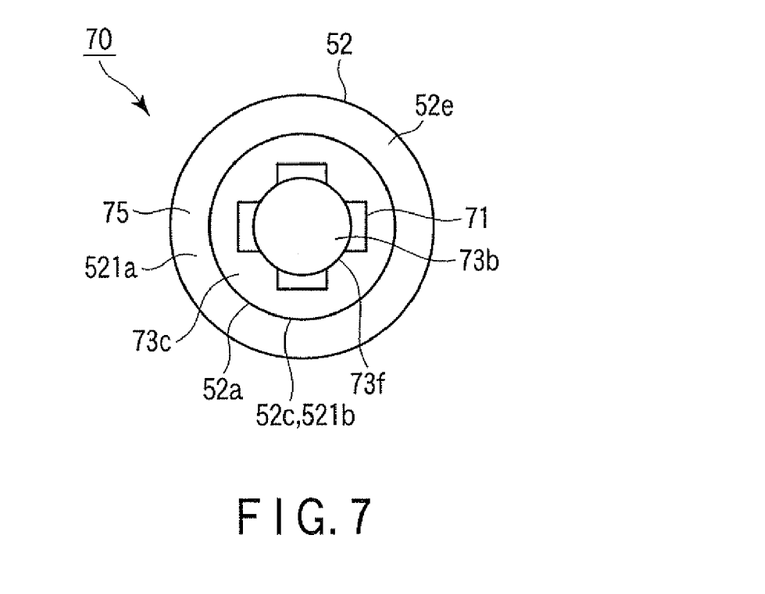
FIG. 7 is a front view of an illumination unit in a modification.

Moreover, although the holding member 73 has a columnar shape in this embodiment, the present invention is not restricted thereto as long as the illumination sections 71 can be held, and the holding member 73 may have, e.g., a rod (cylindrical) shape as shown in FIG. 7.

Additionally, in this embodiment, desired light distribution characteristics can be obtained by setting the inclination angle of the illumination sections 71 to a desired angle, thereby illuminating the observation target with higher brightness.

Further, in this embodiment, the shape of the proximal end portion 73c is not restricted as long as the distal end portion 73b can be inserted in the cylindrical portion 521b and the proximal end portion 73c can be engaged with the cylindrical portion 521b.

It is to be noted that the reflective member 75 does not have to be arranged as a member as long as it can reflect the illumination light in each of the foregoing embodiments. In this case, the reflective member 75 may be the mirror-polished inner peripheral surfaces 52e and 73e or a reflective coating material applied to the inner peripheral surfaces 52e and 73e.

Figure 8A:
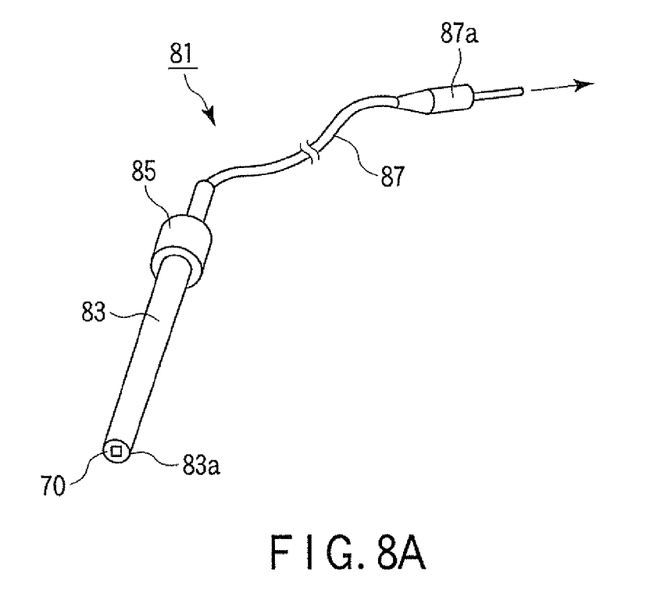
FIG. 8A is a perspective view of an illumination probe having the illumination unit.

Furthermore, the endoscope 12 shown in FIG. 1 and an illumination probe 81 shown in FIG. 8A that can be inserted into an endoscopic channel may have at least one of the illumination units 70 according to the first embodiment and the second embodiment.

When a sufficient amount of light cannot be obtained from the illumination light emitted from the endoscope 12, the illumination probe 81 shown in FIG. 8A is used as auxiliary illumination equipment that supplements the illumination light. When the illumination probe 81 is used, it is inserted from, e.g., a medical instrument insertion opening 37a to run through a medical instrument insertion channel which is an endoscopic channel like the above-described non-illustrated endoscopic medical instrument. The illumination probe 81 is pushed in to the distal end hard section 21 side and then protruded from a non-illustrated distal end opening portion of the medical instrument insertion channel arranged in the distal end hard section 21. Moreover, the illumination probe 81 is connected to a non-illustrated light source device to emit illumination light.

In more detail, the illumination probe 81 has, e.g., an insertion section 83 which is inserted from the medical instrument insertion opening 37a to run through the medical instrument insertion channel as the endoscopic channel, a grasping section 85 which is provided at a proximal end portion of the insertion section 83 used for grasping the illumination probe 81, and an optical cable 87 having a connector 87 as a connecting portion connected with a non-illustrated light source device.

Figure 8B:
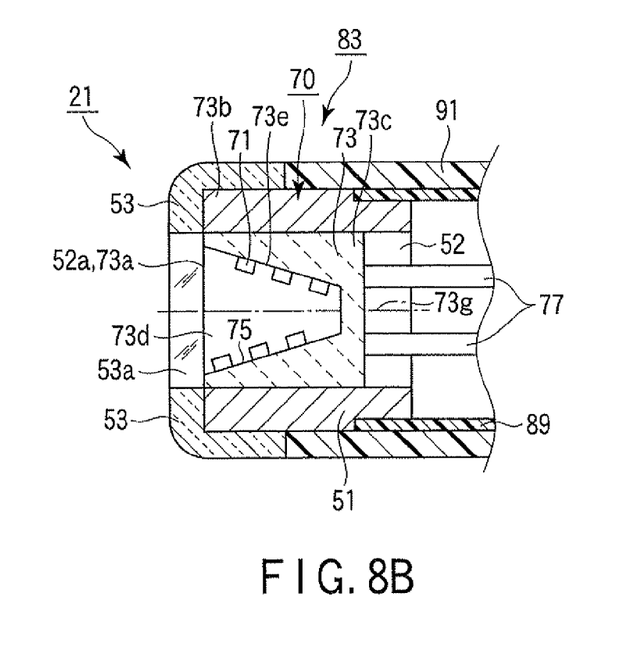
FIG. 8B is a schematic view showing the illumination unit in the illumination probe.

As shown in FIG. 8B, the insertion section 83 has a flexible member 89 as a tubular member having flexibility, an envelope 91 such as a resin covering the flexible member, and a distal end hard section 21 which is a distal end portion 83a of the insertion section 83 (the illumination probe 81). The insertion section 83 has one of the illumination units 70 according to the first and second embodiments at the distal end hard section 21 as shown in FIG. 8B.

The present invention is not restricted to the foregoing embodiments as they are, and constituent elements can be modified and embodied without departing from the essence on the embodying stage. Further, various inventions can be formed by appropriately combining a plurality of constituent elements disclosed in the foregoing embodiments.

Although the preferred embodiments and modifications according to the present invention have been described, the present invention is not restricted thereto. Furthermore, these embodiments and modifications can be combined in many ways.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An illumination unit comprising:
   a hollow member having a through opening;
   a plurality of illumination sections configured to emit illumination light;
   a holding member which is arranged in the through opening and holds the illumination sections to incline the illumination sections at a desired angle with respect an opening surface of the through opening and to form a cascade along the axial direction of the through opening, wherein the holding member holds the illumination sections in such a manner that the illumination sections form a zigzag pattern in a width direction orthogonal to the axial direction of the through opening without facing each other in the width direction; and a reflective member which is configured to reflect the illumination light emitted from the illumination sections toward the opening surface, the reflective member being held by the holding member to face the illumination sections and to apply the illumination light externally emitted from the illumination sections from the inside of the through opening via the opening surface, or being arranged on an inner surface of the through opening to face the illumination sections and to apply the illumination light externally emitted from the illumination units from the inside of the through opening via the opening surface.

2. The illumination unit according to claim 1, wherein the holding member has a holding member opening portion having a tapered shape which is narrowed from a distal end portion of itself toward a proximal end portion of the same along the axial direction of the through opening, and the holding member directly holds the illumination sections and the reflective member on an inner peripheral surface of the holding member opening portion.

3. The illumination unit according to claim 2, wherein the holding member directly holds the plurality of illumination sections on the inner peripheral surface of the holding member opening portion in such a manner that the plurality of illumination sections are inclined at a desired angle with respect to the opening surface and face the inner peripheral surface of the holding member opening portion, and the holding member directly holds the reflective member on the inner peripheral surface of the holding member opening portion in such a manner that the illumination sections emit the illumination light toward the reflective member.

4. The illumination unit according to claim 3, wherein the reflective member is arranged on the entire inner peripheral surface of the holding member opening portion and has a tapered shape which is narrowed from the distal end portion toward the proximal end portion along the axial direction of the through opening in accordance with the shape of the holding member opening portion.

5. The illumination unit according to claim 4, wherein the holding member holds the illumination sections in such a manner that the illumination sections are arranged in a radial pattern extending from the proximal end portion side toward the distal end portion side when the holding member is seen from the front side.

6. The illumination unit according to claim 1, wherein the through opening has a tapered portion having a tapered shape which is radially narrowed from a distal end portion of itself toward a proximal end portion of the same along the axial direction of the through opening, and the holding member is arranged in the through opening and holds the plurality of illumination sections in a state that the illumination sections face the inner peripheral surface of the through opening.

7. The illumination unit according to claim 6, wherein the reflective member is arranged on the entire inner peripheral surface of the through opening and has a tapered shape which is radially narrowed from the distal end portion of the through opening toward the proximal end portion of the through opening along the axial direction of the through opening in accordance with the through opening.

8. The illumination unit according to claim 7, wherein the holding member has a columnar shape or a rod shape and holds the illumination sections on an outer peripheral surface.

9. The illumination unit according to claim 8, wherein the reflective member is arranged in the tapered portion to surround the illumination section.

10. The illumination unit according to claim 1, wherein the plurality of illumination sections emit illumination light in different color wavelength bands.

11. An endoscope comprising an illumination unit according to claim 1.

12. An illumination probe comprising an illumination unit according to claim 1, the illumination probe being configured to be inserted into an endoscopic channel.

* * * * *